(12) United States Patent
Ieko et al.

(10) Patent No.: US 9,977,038 B2
(45) Date of Patent: *May 22, 2018

(54) METHOD FOR DETECTING LUPUS ANTICOAGULANTS

(75) Inventors: Masahiro Ieko, Sapporo (JP); Chizuru Morikawa, Tokyo (JP)

(73) Assignees: SCHOOL JURIDICAL PERSON HIGASHI-NIPPON-GAKUEN, Ishikari-gun (JP); SEKISUI MEDICAL CO., LTD., Tokyo (JP)

( * ) Notice: Subject to any disclaimer, the term of this patent is extended or adjusted under 35 U.S.C. 154(b) by 416 days.

This patent is subject to a terminal disclaimer.

(21) Appl. No.: 14/127,026

(22) PCT Filed: Jun. 15, 2012

(86) PCT No.: PCT/JP2012/065433
§ 371 (c)(1),
(2), (4) Date: Jan. 10, 2014

(87) PCT Pub. No.: WO2012/173259
PCT Pub. Date: Dec. 20, 2012

(65) Prior Publication Data
US 2014/0127725 A1    May 8, 2014

(30) Foreign Application Priority Data
Jun. 17, 2011 (JP) ................. 2011-135173

(51) Int. Cl.
G01N 33/86 (2006.01)
C12Q 1/56 (2006.01)
G01N 33/564 (2006.01)

(52) U.S. Cl.
CPC .............. *G01N 33/86* (2013.01); *C12Q 1/56* (2013.01); *G01N 33/564* (2013.01); *G01N 2800/104* (2013.01); *G01N 2800/24* (2013.01)

(58) Field of Classification Search
CPC .............. C12Q 1/56; G01N 2800/104; G01N 2800/24; G01N 33/564; G01N 33/86
See application file for complete search history.

(56) References Cited

U.S. PATENT DOCUMENTS

| 4,877,741 A | 10/1989 | Babcock et al. | |
|---|---|---|---|
| 5,543,145 A * | 8/1996 | Saint-Remy ......... | A61K 39/395 424/130.1 |
| 2007/0026467 A1 | 2/2007 | Greenfield et al. | |

FOREIGN PATENT DOCUMENTS

| CN | 101221189 A | 7/2008 |
|---|---|---|
| CN | 102066947 A | 5/2011 |
| EP | 1 562 047 A1 | 8/2005 |

OTHER PUBLICATIONS

Bennett, M. (1926) Journal of Biological Chemistry 69: 693-696.*
Medicago catalog excerpt obtained Sep. 5, 2017 (http://www.medicago.se/hepes-buffered-saline-hbs-ph-74).*
Kagawa, K. "Blood Coagulation Correction Test", Examination and Technology, vol. 34, No. 8, pp. 735-742 and 806, (Aug. 1, 2006) (with partial English translation).
Ieko, M. et al., "Cross-Mixing Test to Detect Lupus Anticoagulant for Diagnosis of Antiphospholipid Syndrome", The Japanese Journal of Clinical Pathology, vol. 57, No. 10, pp. 990-998 and 1026, (Oct. 25, 2009) (with partial English translation).
Kanno, N. et al. "Lupus Anticoagulant Sokutei no Tameno Kessho Kentai Sakusei to Kensa no Genjo", Laboratory Practice, Modern Medical Laboratory, vol. 37, No. 13, pp. 1484-1490 and 1508, (Dec. 1, 2009).
Wilson, W.A. et al., "International Consensus Statement on Preliminary Classification Criteria for Definite Antiphospholipid Syndrome", Arthritis & Rheumatism, vol. 42, No. 7, pp. 1309-1311, (Jul. 1999).
Pengo, V. et al., "Update of the guidelines for lupus anticoagulant detection", Journal of Thrombosis and Haemostasis, 7:, pp. 1737-1740, (2009).
International Search Report dated Sep. 25, 2012 in PCT/JP12/065433 Filed Jun. 15, 2012.
Written Opinion of the International Searching Authority dated Sep. 25, 2012 in PCT/JP12/065433 Filed Jun. 15, 2012.
Combined Chinese Office Action and Search Report dated Dec. 30, 2015 in Patent Application No. 201280029871.5 (with English translation of Categories of Cited Documents).
The Extended European Search Report dated Jan. 23, 2015, in Application No. / Patent No. 12800902.4-1404 / 2722674.
Armando Tripodi, "Laboratory Testing for Lupus Anticoagulants: A Review of Issues Affecting Results", Clinical Chemistry, vol. 53, No. 9, XP055161670, Sep. 1, 2007, pp. 1629-1635.
Jun Teruya, et al., "Lupus Anticoagulant Assays : Questions answered and to be answered", Archives of pathology & laboratory medicine, vol. 131, XP055161669, Jun. 1, 2007, pp. 885-889, Retrieved from the Internet: URL:http://www.ncbi.nlm.nih.gov/pubmed/17550315.
U.S. Appl. No. 14/127,041, filed Jan. 10, 2014, Ieko, et al.
Combined Office Action and Search Report dated Jun. 12, 2015 in Chinese Patent Application No. 201280029871.5.

(Continued)

*Primary Examiner* — Lisa J Hobbs
(74) *Attorney, Agent, or Firm* — Oblon, McClelland, Maier & Neustadt, L.L.P.

(57) ABSTRACT

Provided is the development of a convenient LA detection method in which even a sample derived from a patient who receives anticoagulant therapy of warfarin, heparin or the like, is not affected by the anticoagulant therapy, discrimination from the deficiency of blood coagulation factors is enabled, and healthy person's plasma is not used. The method for detecting lupus anticoagulant includes the following steps (A), (B) and (C): (A) a step of adding a buffer solution composition containing blood coagulation factors to each of a blood sample and a diluted sample of the blood sample before measurement or at the time of measurement of the blood coagulation time; (B) a step of measuring the blood coagulation times for the various samples of step (A); and (C) a step of comparing the blood coagulation times for the various samples obtained in step (B).

16 Claims, No Drawings

(56) References Cited

OTHER PUBLICATIONS

Balasch J., et al., "Lupus anticoagulant as a marker of autoimmunity in recurrent pregnancy loss; a case report", Eur. J. Obstet Gynecol Reprod Biol., Oct. 8, 1991;41(3):237-41., 1 page (reference not available, submitting Abstract only).

Jouhikainen T. et al., "Lupus anticoagulant as a prognostic marker in systemic lupus erythematosus", Br J. Rheumatol. Jul. 1993;32(7):568-73. 1 page (reference not available, submitting Abstract only).

Colaco CB, et al.,"The lupus anticoagulant. A disease marker in antinuclear antibody negative lupus that is cross-reactive with autoantibodies to doublestranded DNA", Arthritis Rheum. Jan. 1985;28(1):67-74. 1 page (reference not available, submitting Abstract only).

* cited by examiner

METHOD FOR DETECTING LUPUS ANTICOAGULANTS

TECHNICAL FIELD

The present invention relates to a method for detecting lupus anticoagulant positivity that is used in the diagnosis of the antiphospholipid antibody syndrome.

BACKGROUND ART

Lupus anticoagulant (LA) is a circulating anticoagulant that has been reported for the first time in SLE (Systemic Lupus Erythematosus) patients. In the case of LA-positive patients, from a clinical standpoint, bleeding diathesis is barely recognized, and the patients rather exhibit thrombotic diathesis. However, in the case of samples derived from LA-positive patients, a tendency of prolongation of the activated partial thromboplastin time (APTT) or the prothrombin time (PT) is exhibited in vitro. From the research that followed, it was made clear that LA is an autoantibody to complexes of phospholipids having negative charges and proteins in blood such as β2-glycoprotein I (β2GPI) or prothrombin, and currently it is known that LA is detected in large quantities even in diseases other than SLE. Particularly, the frequency of occurrence is high in the pathologic conditions of diseases that are generically referred to as "antiphospholipid syndrome (APS)", and LA is considered as one of the laboratory findings in connection with the diagnostic criteria for the diseases (Non-Patent Document 1).

LA is defined as an immunoglobulin which inhibits phospholipid-dependent coagulation reactions in vitro (APTT, kaolin clotting time, dilute Russell's viper venom time, and the like), without inhibiting the individual coagulation factor activities, and LA is not a single antibody. For example, as some examples of antibodies responsible for LA, anti-cardiolipin-β2GPI complex antibody, anti-phosphatidylserine-prothrombin complex antibody and the like have been found, and there are measurement systems based on the ELISA method. However, the existence of antibodies responsible for LA other than these is not denied, and even if all of these already known responsible antibodies are negative, there still are cases in which LA becomes positive.

As the reagents for LA detection, reagents for blood coagulation time measurement containing phospholipids are generally used. When LA is contained in a specimen, LA binds with phospholipids in the reagent. Therefore, phospholipids required to advance the coagulation reaction in vitro become insufficient, and the blood coagulation time is prolonged. Accordingly, LA positivity can be determined based on the prolongation of the blood coagulation time. Examples of the reagents for LA detection include reagents for APTT, PT, and dilute Russell's viper venom time (dRVVT).

Furthermore, a blood coagulation correction test (hereinafter, also referred to as "blending test" or "mixing test") in which a reagent for blood coagulation time measurement containing phospholipids is used, normal plasma is added to a test plasma, and the extent of the blood coagulation time of the test plasma being corrected (normalized) is plotted to determine the cause, has also been carried out (Non-Patent Document 2).

As a commercially available reagent for LA detection, a reagent for dRVVT-based analysis called LA test "GRADIPORE" (manufactured by Medical & Biological Laboratories Co., Ltd.) is used. With this reagent, the presence or absence of LA in a specimen is determined on the basis of the ratio of the coagulation time taken by addition of Russell's viper venom and the coagulation time taken by addition of Russell's viper venom and an excessive concentration of phospholipids.

Furthermore, in addition to the reagent described above, a reagent for LA detection called STACLOT LA (manufactured by Diagnostica Stago, Inc.) is also commercially available. With this reagent, the presence or absence of LA in a specimen is determined by examining the difference in the coagulation time for APTT between a sample obtained by adding normal plasma and excess phospholipids to the test plasma, and a sample obtained by adding only normal plasma to the test plasma.

However, in the existing methods described above, it is difficult to discriminate whether the cause of prolongation of the coagulation time lies simply in the deficiency of coagulation factors, in the inhibitors of the coagulation factors, or in LA, only by measuring a single item using each of the reagents. On the other hand, since the therapeutic strategy may vary depending on the difference in the cause, discrimination thereof is important. Therefore, these LA detection methods are rarely used singly, and it is recommended to combine two or more kinds of examinations and comprehensively determine the results (Non-Patent Document 3).

DOCUMENT OF RELATED ART

Non-Patent Document

Non-Patent Document 1: INTERNATIONAL CONSENSUS STATEMENT ON PRELIMINARY CLASSIFICATION CRITERIA FOR DEFINITE ANTIPHOSPHOLIPID SYNDROME, ARTHRITIS & RHEUMATISM Vol. 42, No. 7, July 1999, pp. 1309-1311

Non-Patent Document 2: *Kensa to Gijutsu* (Examination and Technology), Vol. 34, No. 8, August 2006, pp. 735-742

Non-Patent Document 3: Update of the guidelines for lupus anticoagulant detection, Journal of Thrombosis and Haemostasis, 7: pp. 1737-1740 (2009)

DISCLOSURE OF INVENTION

Problem to be Solved by the Invention

As described above, there has been a problem that in order to perform LA detection, several examinations have to be combined making the detection procedure cumbersome and complicated, and training is needed even for an interpretation of the results. For example, when the determination of positivity or negativity gives different results in different kinds of LA detection methods, an analysis considering the principles of the various detection methods is required, and the determination of positivity or negativity has to be made based on the possibility of false negativity or false positivity of the various detection methods. Therefore, it has been very difficult to clearly discriminate the presence or absence of LA in the existing LA detection methods.

Furthermore, many of LA-positive patients exhibit thrombosis symptoms, and in many cases, at the time point where LA is suspected and an examination is initiated, the patients may have already received anticoagulant therapy. However, in the case of samples derived from patients who have received anticoagulant therapy, it is known that false positivity may occur in the APTT and dRVVT, while false negativity may occur in the mixing test.

In the anticoagulant therapy, heparin that has prompt efficacy at the time of emergency and thus can be intravenously administered is used, and in the prevention based on long-term administration, warfarin that is a peroral anticoagulant is used. Warfarin suppresses biosynthesis of Factor II (prothrombin), Factor VII, Factor IX, and Factor X among blood coagulation factors in the liver by antagonizing the action of vitamin K. Therefore, in the case of warfarin taker, since the activity of these coagulation factors is decreased, APTT, PT or dRVVT is greatly prolonged irrespective of the presence or absence of LA. Furthermore, in the mixing test, there are occasions in which patients are considered as factor deficiency type irrespective of the presence or absence of LA. Also, since heparin activates antithrombin and activates the anticoagulation action to thereby suppress coagulation, heparin greatly prolongs the coagulation time irrespective of the presence or absence of LA.

Therefore, it is recommended by the International Society on Thrombosis and Haemostasis (ISTH) that at the time of LA detection, in samples derived from warfarin-administered patients, measurement be made after the test plasma is mixed with an equal amount of a healthy person's plasma in order to supplement any insufficient coagulation factors. Regarding the healthy person's plasma, plasmas that have been subjected to double centrifugation so that the number of blood platelets is less than $10^7$/mL, and have been conditioned such that the activity of all of the blood coagulation factors is almost 100%, are home-made in various facilities and used (Non-Patent Document 3). However, among the blood coagulation factors, there are factors which have very unstable activity and are prone to be inactivated. Thus, it is very difficult to prepare such a healthy person's plasma, and there is a problem that stable acquisition thereof is not easy.

Furthermore, in the preparation of the healthy person's plasma, as the number of people whose plasmas are stored (pool) and mixed increases, the variations in individuals of the activity of the coagulation factors can be averaged. However, the required number of healthy people cannot be secured in some facilities, and since deviations occur in the plasma suppliers, there is a problem that differences in the product quality may occur among different batches. Furthermore, in the method of using a healthy person's plasma, not only the LA in the test plasma is diluted, but also substances that inhibit the measurement of LA contained in the healthy person's plasma (phospholipids, platelet-derived disrupted membranes, and the like) may be incorporated. Therefore, particularly in the case where LA is weakly positive, there is a problem that there is a possibility of false negativity being detected.

Even during the period in which thrombosis symptoms are suppressed by anticoagulant therapy, discrimination of the causes for the thrombosis symptoms is important because the therapeutic strategy is dependent thereon. Furthermore, even in the case where LA positivity is initially detected and anticoagulant therapy is initiated, monitoring of the increase and decrease of LA is considered very useful. However, currently, a method by which the monitoring is conveniently realized does not exist.

Therefore, there has been a strong demand for the development of a convenient method for LA detection in which even for a sample derived from a patient who receives anticoagulant therapy using warfarin or heparin, discrimination from the deficiency of blood coagulation factors can be achieved without being affected by the anticoagulant therapy, and healthy person's plasma is not used.

Means for Solving Problem

Thus, the inventors of the present invention conducted various investigations in order to solve the problems described above, and as a result, the inventors found that when a blood sample and a diluted sample thereof are prepared, a buffer solution composition containing blood coagulation factors (hereinafter, also referred to as an auxiliary reagent) is added to each of the samples before measurement or at the time of measurement of the blood coagulation time of each of the samples, the blood coagulation time is measured for each of the samples, and the blood coagulation times for those samples are compared, LA can be detected with more satisfactory sensitivity and specificity than the conventional methods, without being affected by anticoagulant therapy. Thus, the inventors completed the present invention.

Specifically, the present invention provides a method for detecting lupus anticoagulants, the method including the following steps (A), (B) and (C):

(A) adding a buffer solution composition containing blood coagulation factors to each of a blood sample and a diluted sample of the blood sample before measurement or at the time of measurement of blood coagulation time;

(B) measuring the blood coagulation times for the various samples of step (A); and (C) comparing the blood coagulation times for the various samples obtained in step (B).

Effect of the Invention

According to the present invention, even for a sample derived from a patient who is receiving anticoagulant therapy using warfarin, heparin or the like, the presence or absence of LA can be specifically confirmed conveniently with higher sensitivity than the conventional methods, without being affected by the anticoagulant therapy. Therefore, there is no need to pay attention to whether or not the patient is receiving anticoagulant therapy. Also, since it is not necessary to prepare healthy person's plasma for the measurement of coagulation time for LA detection, the problems of the difference between different batches of healthy person's plasma, which has been conventionally a problem, and stable acquisition can be solved.

BEST MODE FOR CARRYING OUT THE INVENTION

The LA detection method of the present invention is characterized by carrying out the steps (A), (B) and (C). More particularly, the LA detection method is characterized in that a blood sample and a diluted sample of the blood sample (hereinafter, also simply referred to as diluted sample) are used as measurement samples, a buffer solution composition containing blood coagulation factors is added to each of the samples, subsequently the blood coagulation times are measured, and the coagulation times of the samples are compared. In the case of a LA-negative patient, since the amount of coagulation factors is decreased in the diluted sample, the coagulation time is prolonged as compared with the sample that is not diluted. In the case of a LA-positive patient, since the diluted sample has a decreased amount of coagulation factors as well as a decreased amount of LA, the amount of phospholipids that are not bound with LA in the reagent increases, and thus, a reaction by which the coagulation time is prolonged and a reaction by which the coagulation time is shortened, as compared with a sample that is not diluted, occur simultaneously. When the titer of LA (antibody) for capturing phospholipids is high, the coagulation time is shortened as compared with a sample that is not diluted.

The blood sample that is used in the method of the present invention is preferably whole blood or plasma, and usually, the blood sample is prepared by adding an anticoagulant such as sodium citrate to the blood collected from a subject.

Among such blood samples, in the case of dealing with blood samples derived from those subjects for whom conventional LA detection has been difficult, the present invention is particularly useful. Examples of such a blood sample include blood samples of warfarin takers, people who receive anticoagulant therapy such as heparin therapy, people who suffer from vitamin K deficiency, and liver failure patients.

The dilution ratio of the diluted sample is preferably 1.1 times or more, more preferably 1.1 to 3 times, and even more preferably 1.5 to 3 times. The diluent liquid used for the dilution of the blood sample is preferably a buffer solution. Meanwhile, when the blood sample has been diluted in advance, the diluted sample is used after being further diluted.

In step (A) of the method of the present invention, a buffer solution composition containing blood coagulation factors is added to both a blood sample and a diluted sample. When the coagulation time is measured in a sample obtained by diluting the plasma of a LA-positive patient, prolongation of the coagulation time caused by a decrease in the coagulation factor activity and shortening of the coagulation time caused by dilution of LA are both antagonized. When the coagulation factor activity of the patient plasma has been decreased due to warfarin administration or the like, prolongation of the coagulation time is likely to be predominant. Accordingly, in the present invention, in order to suppress the prolongation of the coagulation time caused by a decrease in the coagulation factor activity, and in order to increase the sensitivity to LA, a buffer solution composition containing blood coagulation factors is added to both the blood sample and the diluted sample.

Regarding the blood coagulation factors that are contained in the buffer solution composition used in the present invention, the blood coagulation factors that are considered to be deficient in the blood sample to be tested, or the coagulation factors that are involved in the measurement reaction of the reagent for blood coagulation time measurement used are appropriately selected and used. Specifically, the blood coagulation factors include at least one of blood coagulation factors selected from FII, FV, FVII, FVIII, FIX, FX, FXI and FXII. Furthermore, the blood coagulation factors preferably include one kind or two or more kinds selected from FII, FVII, FVIII, FIX, FX, FXI and FXII, and more preferably include at least one kind or two or more kinds selected from FII, FVII, FIX and FX. Furthermore, in the case of measuring the PT, the blood coagulation factors preferably include one kind or two or more kinds selected from FII, FVII and FX. In the case of measuring the APTT, the blood coagulation factors preferably include one kind or two or more kinds selected from FII, FVIII, FIX, FX, FXI and FXII, and particularly preferably include one kind or two or more kinds selected from FII and FIX. Also, in the case of measuring the dRVVT, the blood coagulation factors preferably include one kind or two or more kinds selected from FII and FX.

The concentration of the coagulation factors is, after a buffer solution composition has been added to the blood sample to be tested, preferably 0.01 U/mL to 2.0 U/mL, and more preferably 0.1 U/mL to 1.0 U/mL. For example, in the case of mixing the blood sample to be tested and the buffer solution composition at a proportion of 9:1, the concentration of the coagulation factors in the buffer solution composition is preferably 0.1 U/mL to 20 U/mL, and more preferably 1 U/mL to 10 U/mL.

The pH of the buffer solution may be any pH that does not deactivate the blood coagulation factors contained in the auxiliary reagent, and the pH is preferably pH 6 to 9, and more preferably pH 6.5 to 8.0. Regarding the buffer solution, any known buffer solution, such as a good buffer solution such as HEPES, can be appropriately used. The concentration of the buffer solution may be any concentration at which the buffering capacity during storage is maintained, and the concentration is preferably 5 mM to 100 mM, and more preferably 5 mM to 50 mM.

Furthermore, in the auxiliary reagent, any compound known as a stabilizer of blood coagulation factors may be appropriately added. For example, glycylglycine, glycylglycylglycine and the like that are disclosed in Japanese Patent Application Publication (JP-B) No. 06-050999 may be added.

In the method of the present invention, a buffer solution composition containing the blood coagulation factors described above is added to a blood sample and a diluted sample before measurement or at the time of measurement of the blood coagulation time. Here, addition of a buffer solution composition before measurement of the blood coagulation time corresponds to a pretreatment of the blood sample and the diluted sample. That is, the buffer solution composition is added to a blood sample and a diluted sample to pretreat the blood sample and the diluted sample, and then the blood coagulation time is measured using a reagent for blood coagulation measurement. On the other hand, addition of a buffer solution composition at the time of measurement of the blood coagulation time corresponds to a process of adding the buffer solution composition to a portion of the reagent for blood coagulation measurement and measuring the blood coagulation time. Between these timings of addition, it is preferable to add the buffer solution composition to the blood sample and the diluted sample before the measurement of the blood coagulation time, from the viewpoint that storage stability of the coagulation factors incorporated in the buffer solution composition is easily secured.

Regarding the reagent for blood coagulation time measurement, any phospholipid-dependent reagent for blood coagulation time measurement or measuring method exhibiting sensitivity to LA may be used, and any known reagent for measuring the prothrombin time (PT), activated partial thromboplastin time (APTT), diluted PT (dPT), diluted APTT (dAPTT), kaolin clotting time (KCT), diluted Russell's viper venom time (dRVVT) and the like can be used. These known reagents are prepared by appropriately combining phospholipids such as cephalin, contact factor-activating agents containing a negatively charged body such as kaolin as a main component, compounds inducing $Ca^{2+}$ such as calcium chloride, viper venom, and the like; according to the principle of measurement. Regarding the form of the reagent, a dried state that is dissolved at the time of use, a solution state, or the like can be appropriately selected. For the reagents described above, commercially available products can be used in all cases. Examples of the reagents for PT measurement that are commercially available include COAGPIA (registered trademark) PT-N (manufactured by SEKISUI MEDICAL CO., LTD.), THROMBOCHECK PT PLUS (manufactured by Sysmex Corp.), and STA Reagent Series PT (manufactured by Roche Diagnostics GmbH). Examples of the reagents for APTT measurement that are commercially available include COAGPIA (registered trademark) APTT-N (manufactured by SEKISUI MEDICAL CO., LTD.), THROMBOCHECK APTT-SLA (manufactured by Sysmex Corp.), APTT Liquid "RD" and PTT-LA reagent "RD" (manufactured by Roche Diagnostics GmbH). Examples of the reagents for dRVVT measurement that are commercially available include LA Test "GRADIPORE" (manufactured by Medical & Biological Laboratories Co., Ltd.). Furthermore, one or more of these reagents and the buffer solution composition containing blood coagulation factors of the present invention (auxiliary reagent) may be combined and used as a reagent kit for LA detection.

As a method of comparing the coagulation times of a blood sample and a diluted sample, the ratio can be calculated. For example, in the case of taking the coagulation time of the blood sample as a reference, the ratio is calculated by the following formula:

Ratio=(Coagulation time of diluted sample)/(coagulation time of blood sample)

In this case, as the ratio is larger, since the coagulation time of the diluted sample is prolonged, it is considered to be LA-negative. As the ratio is smaller, it is considered to be LA-positive.

The cut-off value for determining negativity or positivity is desirably calculated statistically by a general method from the measured values of healthy persons' plasmas with no coagulation abnormality. For example, the average value and standard deviation (SD) are determined from the measured values of the plasmas of 20 or more healthy persons, and the value of (average value+2SD (depending on cases, average value−2SD)) is calculated. Alternatively, the cut-off value is determined by a percentile method.

HEPES at pH 7.5, and 150 mM sodium chloride) (plasma 25 μL: HBS 20 μL), and APTT is measured using this mixture as a sample (condition 2). When the APTT of condition 1 is defined as A seconds, and the APTT of condition 2 is defined as B seconds, B/A (ratio) is calculated as a measured value for determination. In Inventions 1 and 2 that will be described below, since the presence or absence of LA is discriminated on the basis of the shortening of the coagulation time at the time of dilution, a smaller ratio represents positivity. Regarding the cut-off value for determination, the value of (measured value of plasma of 20 or more healthy persons−2SD) was used.

TABLE 1

| | Measurement parameters | | | | | | | |
|---|---|---|---|---|---|---|---|---|
| | Test plasma | HBS | Auxiliary reagent | | APTT reagent | | Calcium chloride solution |
| Measurement condition 1 | 45 μL | — | 5 μL | →Incubated→ | 50 μL | →Incubated→ | 50 μL |
| Measurement condition 2 | 25 μL | 20 μL | 5 μL | →Incubated→ | 50 μL | →Incubated→ | 50 μL |

EXAMPLES

The present invention will be described in more detail by the following Examples, but the present invention is not intended to be limited to the following Examples.

<Items of Measurement>
(1) APTT Screening Test
Measurement was carried out using a PTT LA reagent, "RD" (manufactured by Diagnostica Stago, Inc.), and an automatic blood coagulation analyzer, STA-R (manufactured by Roche Diagnostics GmbH). Regarding the cut-off value for determination, the value of (measured value of 20 or more healthy persons+2SD) was used.

(2) dRVVT Test
Measurement was carried out using LA Test "GRADI-PORE" (manufactured by Medical & Biological Laboratories Co., Ltd.) and an automatic blood coagulation analyzer, STA-R. Regarding the cut-off value for determination, the value of (measured value of 20 or more healthy persons+2SD) was used.

(3) Mixing Test
Measurement was carried out using a PTT LA reagent, "RD" (manufactured by Diagnostica Stago, Inc.) and an automatic blood coagulation analyzer, CP2000 (manufactured by SEKISUI MEDICAL CO., LTD.). As normal plasma, Pooled Normal Plasma (hereinafter, PNP; Precision Biologic, Inc.) was used. The sample mixing proportion was set to 0%, 10%, 20%, 50% and 100%, and measurement was carried out by automatically diluting the sample using the mixing test function of CP2000. Determination was made such that a graph was drawn, and if the graph was convex, the sample was determined to be LA-positive.

(4) Modification of APTT Test (Method of Present Invention)
Measurement was carried out using COAGPIA APTT-N (manufactured by SEKISUI MEDICAL CO., LTD.) and a buffer solution containing the blood coagulation factors that will be described below (hereinafter, auxiliary reagent), and using an automatic blood coagulation analyzer, CP2000 (manufactured by SEKISUI MEDICAL CO., LTD.), with the measurement parameters indicated in Table 1. Specifically, first, 5 μL of the auxiliary reagent is added to 45 μL of the test plasma, and ATPP is measured using this mixture as a sample (condition 1). Next, 5 μL of the auxiliary reagent is added to a dilution of the test plasma with HBS (50 mM <Auxiliary Reagent>
Auxiliary reagent 1 and auxiliary reagent 2 were prepared by adding the blood coagulation factors indicated in Table 2 to HBS (50 mM HEPES pH 7.5, and 150 mM sodium chloride) as a base. For the blood coagulation factors, products manufactured by Haematologic Technologies, Inc. were used in all cases.

Furthermore, in Table 3 to Table 6 that are described below, the results obtained in the case of using the auxiliary reagent 1 are presented as "Invention 1", and the results obtained in the case of using the auxiliary reagent 2 are presented as "Invention 2".

TABLE 2

| Auxiliary reagent composition | | | |
|---|---|---|---|
| | Human Factor II | Human Factor IX | Human Factor VIII |
| Auxiliary reagent 1 | 200 μg/mL | 2 U/mL | — |
| Auxiliary reagent 2 | 200 μg/mL | 2 U/mL | 2 U/mL |

In Table 2 described above, 200 μg/mL of Human Factor II corresponds to 2 U/mL.

<Test Plasma>
Test plasmas A, B and C are plasmas collected from patients who receive warfarin administration. As viewed from the clinical symptoms and the like, the presence of LA is denied.

Test plasmas 1 and 2 are plasmas in which blood coagulation factor VIII and blood coagulation factor IX are deficient. The patients do not receive the administration of an anticoagulant.

Test plasmas 3 to 10 are plasmas collected from patients who receive the administration of heparin, which is an anticoagulant. As viewed from the clinical symptoms and the like, the presence of LA is denied.

Test plasmas 11 to 37 are plasmas collected from patients who are suspected of carrying antiphospholipid antibodies, according to the underlying diseases or clinical symptoms. Among these, plasmas 11 to 24 are plasmas collected from patients who receive warfarin administration.

<Results>

As listed in Table 3, in the warfarin-administered/non-LA group, the result values are all higher than or equal to the cut-off value in the APTT screening test, so that discrimination from LA positivity is difficult. Furthermore, in the dRVVT test, two examples out of three examples showed false positivity (in the table, indicated as "positive*"). On the other hand, the results were all negative in the mixing text and Inventions 1 and 2.

TABLE 3

Determination of warfarin-administered specimens in which presence of LA is denied

| | APTT screening | | dRVVT | | | | Mixing test | Invention 1 | | | | Invention 2 | | | |
|---|---|---|---|---|---|---|---|---|---|---|---|---|---|---|---|
| | sec | Determination | sec | sec | Ratio | Determination | Determination | sec | sec | Ratio | Determination | sec | sec | Ratio | Determination |
| Cut-off value | 48.4 | | | | 1.25 | | | | | 1.30 | | | | 1.35 | |
| Specimen A (warfarin-administered) | 53.1 | Positive | 56.8 | 48.0 | 1.18 | Negative | Negative | 33.7 | 47.8 | 1.42 | Negative | 29.8 | 43.5 | 1.46 | Negative |
| Specimen B (warfarin-administered) | 57.4 | Positive | 77.9 | 54.8 | 1.42 | Positive* | Negative | 33.9 | 49.3 | 1.45 | Negative | 30.3 | 45.8 | 1.51 | Negative |
| Specimen C (warfarin-administered) | 78.7 | Positive | 112.4 | 67.6 | 1.66 | Positive* | Negative | 39.0 | 56.1 | 1.44 | Negative | 34.5 | 53.0 | 1.54 | Negative |

As listed in Table 4, in the plasmas of coagulation factor-deficient (FVIII and FIX) patients in which the presence of LA is denied, the result values were all higher than or equal to the cut-off value in the APTT screening test, so that discrimination from LA positivity is difficult. On the other hand, in the dRVVT test, the mixing test, and Inventions 1 and 2, the result values were all negative. The method of the present invention involves a system in which coagulation factors are supplemented to a test plasma; however, since the method includes a process of comparing the values obtained before and after dilution, the results obtained in a state in which simply coagulation factors are deficient, and the results in the case that is inhibitor-positive are not ambiguous. Discrimination can be made clearly as in the case of the dRVVT test or the mixing test.

TABLE 4

Determination of coagulation factor-deficient plasmas in which presence of LA is denied

| | APTT screening | | dRVVT | | | | Mixing test | Invention 1 | | | | Invention 2 | | | |
|---|---|---|---|---|---|---|---|---|---|---|---|---|---|---|---|
| | sec | Determination | sec | sec | Ratio | Determination | Determination | sec | sec | Ratio | Determination | sec | sec | Ratio | Determination |
| Cut-off value | 48.4 | | | | 1.25 | | | | | 1.30 | | | | 1.35 | |
| Specimen 1 (Factor 8-deficient) | 153.6 | Positive | 33.8 | 36.3 | 0.93 | Negative | Negative | 99.7 | 133.8 | 1.34 | Negative | 36.8 | 57.5 | 1.56 | Negative |
| Specimen 2 (Factor 9-deficient) | 149.2 | Positive | 80.4 | 74.2 | 1.08 | Negative | Negative | 33.3 | 44.2 | 1.33 | Negative | 30.7 | 42.1 | 1.37 | Negative |

As listed in Table 5, in the heparin-administered/non-LA group, the result values in seven examples out of eight examples are all higher than or equal to the cut-off value in the APTT screening test, so that discrimination from LA positivity is difficult. Furthermore, in the dRVVT test, two examples out of eight examples showed false positivity (in the table, indicated as "positive*"). On the other hand, the results were all negative in Inventions 1 and 2.

seven examples out of fourteen examples (in the table, indicated as "Positive*") may be false positive. For three specimen examples which were determined negative in the mixing test but positive in Inventions 1 and 2 (specimens 11, 21 and 23), anti-β2GPI antibody (hereinafter, aβ2GPI) and anti-phosphatidylserine-prothrombin composite antibody (hereinafter, aPS/PT), which may be considered as antibodies responsible for LA, were measured, and specimens 11

TABLE 5

Determination of heparin-administered specimens in which presence of LA is denied

| | APTT screening | | dRVVT | | | | Invention 1 | | | | Invention 2 | | | |
|---|---|---|---|---|---|---|---|---|---|---|---|---|---|---|
| | sec | Determination | sec | sec | Ratio | Determination | sec | sec | Ratio | Determination | sec | sec | Ratio | Determination |
| Cut-off value | 48.4 | | | | 1.25 | | | | 1.30 | | | | 1.35 | |
| Specimen 3 (heparin-administered) | 202.0 | Positive | 48.9 | 43.5 | 1.12 | Negative | 88.2 | 148.0 | 1.68 | Negative | 70.0 | 126.7 | 1.81 | Negative |
| Specimen 4 (heparin-administered) | 96.1 | Positive | 54.0 | 43.6 | 1.24 | Negative | 49.3 | 71.7 | 1.45 | Negative | 42.6 | 65.8 | 1.54 | Negative |
| Specimen 5 (heparin-administered) | e. | Positive | 39.6 | 37.2 | 1.06 | Negative | 45.5 | 71.0 | 1.56 | Negative | 39.9 | 66.1 | 1.66 | Negative |
| Specimen 6 (heparin-administered) | 61.4 | Positive | 60.5 | 47.7 | 1.27 | Positive* | 43.8 | 63.7 | 1.45 | Negative | 38.1 | 60.5 | 1.59 | Negative |
| Specimen 7 (heparin-administered) | 45.6 | Negative | 38.3 | 33.8 | 1.13 | Negative | 40.8 | 64.7 | 1.59 | Negative | 36.3 | 58.0 | 1.60 | Negative |
| Specimen 8 (heparin-administered) | 145.2 | Positive | 64.9 | 46.8 | 1.39 | Positive* | 76.4 | 118.8 | 1.55 | Negative | 61.9 | 100.6 | 1.63 | Negative |
| Specimen 9 (heparin-administered) | 57.1 | Positive | 40.8 | 38.5 | 1.06 | Negative | 47.7 | 73.7 | 1.55 | Negative | 44.6 | 67.6 | 1.52 | Negative |
| Specimen 10 (heparin-administered) | 56.3 | Positive | 41.7 | 36.6 | 1.14 | Negative | 39.8 | 60.2 | 1.51 | Negative | 36.9 | 57.5 | 1.56 | Negative | e.: error departing from measurement range

Table 6 lists the results of a specimen group that is suspected of having LA. In the warfarin-administered group, the results values in thirteen examples out of fourteen examples were higher than or equal to the cut-off value in the APTT screening test; however, when the results of Table 3 are considered, discrimination from LA positivity is difficult. Also, in the dRVVT test, the results of thirteen examples out of fourteen examples were positive; however, since a possibility of inducing false positivity due to warfarin administration is suggested from the results of Table 3, discrimination between false positivity due to warfarin and LA positivity is difficult. Meanwhile, the negative specimen in the APTT screening test (specimen 16) and the negative specimen in the dRVVT test (specimen 19) do not coincide. On the other hand, in the mixing test, the results of three examples out of fourteen examples were positive, and all the three positive examples were positive also in Inventions 1 and 2. Therefore, it is contemplated that there is a high possibility that among the results of the dRVVT test, at least and 21 were positive against both antibodies, while specimen 23 was positive against aPS/PT. From the above results, it is contemplated that there is a very high possibility that the results of these three examples obtained in the mixing test are false negative, and are LA-positive in reality.

In the non-warfarin-administered group, the results of six examples out of thirteen examples were positive in all the items, and the results of two examples were negative. Therefore, in these eight examples, discrimination of positivity/negativity was possible. Among the remaining five examples, aβ2GPI and aPS/PT were measured for specimen 30 that showed positivity only in Inventions 1 and 2. However, since aβ2GPI was positive, it is contemplated that there is a very high possibility that the results for dRVVT and the mixing test are false negative, and are LA-positive in reality.

TABLE 6

Determination of warfarin-administered/non-administered specimens in which presence of LA is suspected

| | Item | | | | | | | | |
|---|---|---|---|---|---|---|---|---|---|
| | APTT screening | | dRVVT | | | Mixing test | Invention 1 | | |
| | Unit | | | | | | | | |
| | sec | Determination | sec | sec | Ratio | Determination | Determination | sec | sec | Ratio |
| Cut-off value | 48.4 | | | | 1.25 | | | | | 1.30 |
| Specimen 11 (warfarin-administered) | 143.0 | Positive | 220.4 | 82.5 | 2.67 | Positive | Negative | 102.5 | 76.4 | 0.75 |
| Specimen 12 (warfarin-administered) | 117.5 | Positive | 126.4 | 55.4 | 2.28 | Positive | Positive | 82.8 | 81.2 | 0.98 |
| Specimen 13 (warfarin-administered) | 71.9 | Positive | 100.4 | 60.3 | 1.67 | Positive* | Negative | 41.2 | 54.6 | 1.33 |
| Specimen 14 (warfarin-administered) | 57.5 | Positive | 72.1 | 57.1 | 1.26 | Positive* | Negative | 33.0 | 51.8 | 1.57 |
| Specimen 15 (warfarin-administered) | 49.4 | Positive | 60.7 | 45.9 | 1.32 | Positive* | Negative | 35.9 | 50.2 | 1.40 |
| Specimen 16 (warfarin-administered) | 48.2 | Negative | 57.6 | 45.3 | 1.27 | Positive* | Negative | 36.8 | 52.8 | 1.43 |
| Specimen 17 (warfarin-administered) | 87.0 | Positive | 99.2 | 49.4 | 2.01 | Positive | Positive | 46.9 | 55.1 | 1.17 |
| Specimen 18 (warfarin-administered) | 52.0 | Positive | 97.8 | 58.8 | 1.66 | Positive* | Negative | 36.3 | 52.7 | 1.45 |
| Specimen 19 (warfarin-administered) | 91.4 | Positive | 75.5 | 64.3 | 1.17 | Negative | Negative | 45.8 | 67.7 | 1.48 |
| Specimen 20 (warfarin-administered) | 88.9 | Positive | 60.7 | 47.7 | 1.27 | Positive* | Negative | 36.4 | 56.1 | 1.54 |
| Specimen 21 (warfarin-administered) | 355.3 | Positive | 221.1 | 71.7 | 3.08 | Positive | Negative | 145.5 | 138.5 | 0.95 |
| Specimen 22 (warfarin-administered) | 74.1 | Positive | 80.1 | 51.8 | 1.55 | Positive | Positive | 57.0 | 66.5 | 1.17 |
| Specimen 23 (warfarin-administered) | 89.3 | Positive | 71.8 | 51.9 | 1.38 | Positive | Negative | 66.3 | 62.3 | 0.94 |
| Specimen 24 (warfarin-administered) | 100.9 | Positive | 74.5 | 52.3 | 1.42 | Positive* | Negative | 46.0 | 70.6 | 1.53 |
| Specimen 25 (no warfarin administration) | 53.4 | Positive | 45.8 | 36.6 | 1.25 | Positive | Negative | 36.1 | 46.8 | 1.30 |
| Specimen 26 (no warfarin administration) | 78.6 | Positive | 92.2 | 40.5 | 2.28 | Positive | Positive | 52.8 | 61.6 | 1.17 |
| Specimen 27 (no warfarin administration) | 39.1 | Negative | 43.3 | 33.4 | 1.30 | Positive | — | 26.9 | 38.6 | 1.43 |
| Specimen 28 (no warfarin administration) | 43.8 | Negative | 42.9 | 37.2 | 1.15 | Negative | — | 40.3 | 53.7 | 1.33 |
| Specimen 29 (no warfarin administration) | 42.7 | Negative | 40.8 | 34.8 | 1.17 | Negative | — | 34.9 | 49.3 | 1.41 |
| Specimen 30 (no warfarin administration) | 38.3 | Negative | 42.0 | 34.2 | 1.23 | Negative | — | 22.9 | 28.9 | 1.26 |
| Specimen 31 (no warfarin administration) | 111 | Positive | 79.3 | 38.4 | 2.07 | Positive | Positive | 53.1 | 63.4 | 1.19 |
| Specimen 32 (no warfarin administration) | 90.5 | Positive | 78.2 | 38.9 | 2.01 | Positive | Positive | 63.0 | 77.0 | 1.22 |
| Specimen 33 (no warfarin administration) | 33.8 | Negative | 39.1 | 31.2 | 1.25 | Positive | — | 23.4 | 33.8 | 1.44 |

TABLE 6-continued

Determination of warfarin-administered/non-administered specimens in which presence of LA is suspected

| | | | | | | | | | | |
|---|---|---|---|---|---|---|---|---|---|---|
| Specimen 34 (no warfarin administration) | 54.9 | Positive | 44.5 | 35.9 | 1.24 | Negative | Negative | 36.1 | 50.9 | 1.41 |
| Specimen 35 (no warfarin administration) | 85.7 | Positive | 82.0 | 42.3 | 1.94 | Positive | Positive | 50.8 | 57.9 | 1.14 |
| Specimen 36 (no warfarin administration) | 80.5 | Positive | 90.1 | 42.6 | 2.12 | Positive | Positive | 46.6 | 46.9 | 1.01 |
| Specimen 37 (no warfarin administration) | 80.0 | Positive | 88.9 | 43.7 | 2.03 | Positive | Positive | 50.3 | 54.4 | 1.08 |

| | Item | | | | | |
|---|---|---|---|---|---|---|
| | Invention 1 | Invention 2 | | | aβ2GPI | aPS/PT |
| | | Unit | | | | |
| | Determination | sec | sec | Ratio | Determination | Determination |
| Cut-off value | | | | 1.35 | | |
| Specimen 11 (warfarin-administered) | Positive | 80.5 | 66.4 | 0.82 | Positive | Positive |
| Specimen 12 (warfarin-administered) | Positive | 70.7 | 72.7 | 1.03 | Positive | |
| Specimen 13 (warfarin-administered) | Negative | 35.6 | 49.6 | 1.39 | Negative | |
| Specimen 14 (warfarin-administered) | Negative | 30.4 | 49.4 | 1.63 | Negative | |
| Specimen 15 (warfarin-administered) | Negative | 32.0 | 45.9 | 1.43 | Negative | |
| Specimen 16 (warfarin-administered) | Negative | 33.1 | 50.3 | 1.52 | Negative | |
| Specimen 17 (warfarin-administered) | Positive | 42.9 | 51.6 | 1.20 | Positive | |
| Specimen 18 (warfarin-administered) | Negative | 34.1 | 50.9 | 1.49 | Negative | |
| Specimen 19 (warfarin-administered) | Negative | 41.6 | 63.8 | 1.53 | Negative | |
| Specimen 20 (warfarin-administered) | Negative | 33.0 | 52.9 | 1.60 | Negative | |
| Specimen 21 (warfarin-administered) | Positive | 113.4 | 121.5 | 1.07 | Positive | Positive |
| Specimen 22 (warfarin-administered) | Positive | 49.3 | 58.5 | 1.19 | Positive | |
| Specimen 23 (warfarin-administered) | Positive | 56.6 | 56.2 | 0.99 | Positive | Negative | Positive |
| Specimen 24 (warfarin-administered) | Negative | 42.3 | 63.1 | 1.49 | Negative | |
| Specimen 25 (no warfarin administration) | Negative | 32.9 | 45.9 | 1.40 | Negative | |
| Specimen 26 (no warfarin administration) | Negative | 49.3 | 58.8 | 1.19 | Negative | |
| Specimen 27 (no warfarin administration) | Negative | 25.8 | 37.6 | 1.46 | Negative | |
| Specimen 28 (no warfarin administration) | Negative | 35.9 | 49.5 | 1.38 | Negative | |

TABLE 6-continued

Determination of warfarin-administered/non-administered specimens in which presence of LA is suspected

| | | | | | | | |
|---|---|---|---|---|---|---|---|
| Specimen 29 (no warfarin administration) | Negative | 32.4 | 46.7 | 1.44 | Negative | | |
| Specimen 30 (no warfarin administration) | Positive | 21.8 | 28.4 | 1.30 | Positive | Positive | Negative |
| Specimen 31 (no warfarin administration) | Positive | 45.2 | 59.1 | 1.31 | Positive | | |
| Specimen 32 (no warfarin administration) | Positive | 54.8 | 71.3 | 1.30 | Positive | | |
| Specimen 33 (no warfarin administration) | Negative | 22.5 | 33.0 | 1.47 | Negative | | |
| Specimen 34 (no warfarin administration) | Negative | 33.3 | 45.8 | 1.38 | Negative | | |
| Specimen 35 (no warfarin administration) | Negative | 44.2 | 52.7 | 1.19 | Negative | | |
| Specimen 36 (no warfarin administration) | Negative | 40.1 | 44.6 | 1.11 | Negative | | |
| Specimen 37 (no warfarin administration) | Negative | 40.7 | 49.6 | 1.22 | Negative | | |

In the APTT screening test and the dRVVT test, the system is affected by anticoagulants such as heparin or warfarin, and induces false positivity. Furthermore, in the mixing test, the system is affected by warfarin or the like, and may induce false negativity. The method of the present invention can achieve clear discrimination from coagulation factor deficiency without being affected by anticoagulants such as heparin or warfarin as in the case of the APTT screening test and the dRVVT test, and exhibits higher sensitivity and less false negativity than the mixing test.

The invention claimed is:

1. A method for detecting lupus anticoagulants, the method comprising:
   (A) adding a composition comprising blood coagulation factors to a blood or plasma sample obtained from a subject that has been given warfarin or heparin, and a sample of the blood or plasma sample diluted of 1.1 to 3 times in a solution buffered at a pH of from 6 to 9 before measurement or at the time of measurement of blood coagulation time, wherein the blood coagulation factors are at least one selected from the group consisting of FII, FV, FVII, FVIII, FIX, FX, FXI and FXII, wherein the composition is not a plasma or blood sample, wherein the composition does not comprise phospholipids,
   wherein the composition is buffered at a pH of from 6 to 9; and
   wherein the composition comprises the blood coagulation factor in an amount of 0.01 U/ml to 2.0 U/ml;
   (B) measuring the blood coagulation times for the blood sample and the diluted sample in an in vitro assay selected from the group consisting of measuring prothrombin time, measuring an activated partial thromboplastin time, measuring a diluted prothrombin time, measuring a kaolin clotting time, and measuring diluted Russell's viper venom time; and
   (C) comparing the blood coagulation times for the blood sample and the diluted sample obtained in (B) to yield a ratio of the blood coagulation time of the diluted sample to the blood sample such that if the ratio is less than the same ratio measured from a healthy subjects blood or plasma indicates the presence of lupus anticoagulants.

2. The detection method according to claim 1, wherein the blood sample is whole blood or plasma.

3. The detection method according to claim 1, wherein the solution buffered at a pH of from 6 to 9 is added to the blood or plasma sample before the measurement of the blood coagulation time.

4. The detection method according to claim 1, wherein the measuring of the blood coagulation time (B) comprises measuring activated thromboplastin time or dilute Russell's viper venom time.

5. The detection method according to claim 2, wherein the solution buffered at a pH of from 6 to 9 is added to the blood or plasma sample before the measurement of the blood coagulation time.

6. The detection method according to claim 2, wherein the measuring of the blood coagulation time (B) comprises measuring activated thromboplastin time or dilute Russell's viper venom time.

7. The detection method according to claim 3, wherein the measuring of the blood coagulation time (B) comprises measuring activated thromboplastin time or dilute Russell's viper venom time.

8. The detection method according to claim 1, wherein the blood coagulation is FII.

9. The detection method according to claim 8, further comprising a second blood coagulation factor that is FX.

10. The detection method according to claim 9, further comprising a second blood coagulation factor that is FV.

11. The detection method according to claim 1, wherein the blood coagulation factors is FV.

12. The detection method according to claim 1, wherein the blood coagulation factors is FX.

13. The detection method according to claim 11, further comprising a second blood coagulation factor that is FX.

14. The detection method according to claim 1, wherein the measuring of the blood coagulation time (B) comprising measuring activated thromboplastin time.

15. The detection method according to claim 1, wherein the measuring of the blood coagulation time (B) comprises measuring dilute Russell's viper venom time.

16. The detection method according to claim 1, wherein the solution buffered at a pH of from 6 to 9 is a HEPES buffer solution.

* * * * *